United States Patent
Tompers et al.

(10) Patent No.: US 9,132,417 B2
(45) Date of Patent: Sep. 15, 2015

(54) METHOD FOR PRODUCING A SUPPORTED HYDROGENATION CATALYST HAVING INCREASED HYDROGENATION ACTIVITY

(75) Inventors: Rolf Tompers, Mannheim (DE); Heiko Urtel, Bobenheim-Roxheim (DE); Rolf Pinkos, Bad Dürkheim (DE); Gerd-Dieter Tebben, Mannheim (DE); Jens Heimann, Worms (DE); Maria Guixa Guardia, Mannheim (DE); Sabine Borchers, Erlenbach Bei Kandel (DE)

(73) Assignee: BASF SE (DE)

( * ) Notice: Subject to any disclaimer, the term of this patent is extended or adjusted under 35 U.S.C. 154(b) by 756 days.

(21) Appl. No.: 13/510,115

(22) PCT Filed: Nov. 16, 2010

(86) PCT No.: PCT/EP2010/067572
§ 371 (c)(1),
(2), (4) Date: May 16, 2012

(87) PCT Pub. No.: WO2011/061185
PCT Pub. Date: May 26, 2011

(65) Prior Publication Data
US 2012/0245394 A1    Sep. 27, 2012

(30) Foreign Application Priority Data

Nov. 17, 2009    (EP) .................................... 09176203

(51) Int. Cl.
| | | |
|---|---|---|
| *B01J 23/72* | (2006.01) | |
| *B01J 23/80* | (2006.01) | |
| *B01J 23/78* | (2006.01) | |
| *B01J 23/58* | (2006.01) | |
| *B01J 23/83* | (2006.01) | |
| *B01J 37/06* | (2006.01) | |
| *C07C 29/141* | (2006.01) | |
| *C07C 29/149* | (2006.01) | |
| *B01J 37/00* | (2006.01) | |

(52) U.S. Cl.
CPC *B01J 23/78* (2013.01); *B01J 23/58* (2013.01); *B01J 23/72* (2013.01); *B01J 23/83* (2013.01); *B01J 37/06* (2013.01); *C07C 29/141* (2013.01); *C07C 29/149* (2013.01); *B01J 23/80* (2013.01); *B01J 37/0063* (2013.01)

(58) Field of Classification Search
CPC .................................. B01J 23/72; B01J 23/80
USPC ........................................................ 502/345
See application file for complete search history.

(56) References Cited

U.S. PATENT DOCUMENTS

| | | |
|---|---|---|
| 4,826,799 A | 5/1989 | Cheng et al. |
| 5,536,694 A | 7/1996 | Schuetz et al. |
| 5,780,686 A | 7/1998 | Holderich et al. |
| 5,780,687 A | 7/1998 | Holderich et al. |
| 5,981,769 A | 11/1999 | Baur et al. |
| 6,008,418 A | 12/1999 | Baur et al. |
| 6,448,457 B1 | 9/2002 | Hesse et al. |
| 7,510,591 B2 | 3/2009 | Huber-Dirr et al. |
| 2002/0058841 A1 | 5/2002 | Ansmann et al. |
| 2008/0071120 A1 | 3/2008 | Houssin et al. |
| 2008/0299390 A1 | 12/2008 | Houssin et al. |
| 2010/0094058 A1 | 4/2010 | Lettmann et al. |
| 2011/0313188 A1 | 12/2011 | Wigbers et al. |

FOREIGN PATENT DOCUMENTS

| | | |
|---|---|---|
| CA | 2614520 A1 | 1/2007 |
| DE | 19607954 A1 | 9/1997 |
| DE | 19607955 A1 | 9/1997 |
| DE | 19647348 A1 | 5/1998 |
| DE | 19647349 A1 | 5/1998 |
| DE | 19809418.3 | 9/1999 |
| DE | 102007011484 A1 | 9/2008 |
| EP | 0648534 A1 | 4/1995 |
| EP | 0810194 A1 | 12/1997 |
| EP | 0810202 A2 | 12/1997 |
| EP | 1207149 A1 | 5/2002 |
| ES | 2192039 T3 | 9/2003 |
| WO | WO-02083818 A2 | 10/2002 |
| WO | WO-2007006719 A1 | 1/2007 |
| WO | WO-2007/028411 A1 | 3/2007 |
| WO | WO-2010089346 A2 | 8/2010 |

OTHER PUBLICATIONS

International Search Report for PCT/EP2010/067572 mailed Aug. 19, 2011.
International Preliminary Report on Patentability for PCT/EP2010/067572 mailed Apr. 20, 2012.

*Primary Examiner* — Elvis O Price
(74) *Attorney, Agent, or Firm* — Drinker Biddle & Reath LLP

(57) ABSTRACT

In a process for preparing a supported hydrogenation catalyst with increased hydrogenation activity, which comprises a hydrogenating metal and/or an oxide of a hydrogenating metal on an $Al_2O_3$-containing support material, said calcined supported hydrogenation catalyst is treated before or after the final shaping thereof and before use thereof in the hydrogenation with a base solution having a pH of >10 at a temperature in the range from 20 to 120° C. for 1 to 300 hours.

12 Claims, No Drawings

METHOD FOR PRODUCING A SUPPORTED HYDROGENATION CATALYST HAVING INCREASED HYDROGENATION ACTIVITY

CROSS-REFERENCE TO RELATED APPLICATIONS

This application is a national stage application (under 35 U.S.C. §371) of PCT/EP2010/067572, filed Nov. 16, 2010, which claims benefit of European Application 09176203.9, filed Nov. 17, 2009.

The invention relates to a process for preparing a supported hydrogenation catalyst with increased hydrogenation activity, to a hydrogenation catalyst obtainable by the process, to the use thereof for hydrogenating organic compounds having carbonyl groups and to a corresponding process for hydrogenating organic compounds having carbonyl groups.

The hydrogenation of organic compounds having carbonyl groups over supported hydrogenation catalysts is known per se. For instance, WO 2007/006719 describes a catalyst and a process for hydrogenating carbonyl compounds. A catalyst prepared by precipitation of a mixture of a copper nitrate solution, an aluminum nitrate solution and a lanthanum nitrate solution with sodium carbonate is used. The precipitated catalyst is dried and calcined, and also compacted. The compactate is mixed with copper flakes and graphite and pressed to tablets. Before use in the hydrogenation, these tablets are pretreated with water or steam. It is specified that the treatment is effected at a temperature of 100 to 140° C. and a pressure of 1 to 30 bar, and the water used can be adjusted to a pH of 4 to 9, preferably 6 to 8.5, with the aid of mineral acids such as nitric acid, sulfuric acid or hydrochloric acid, or sodium carbonate or sodium hydroxide solution.

An enhanced hydrogenation activity and selectivity of the catalyst with retention of a high stability of the shaped body were found.

The starting activity of the catalyst may, however, still be in need of improvement for some applications.

It is therefore an object of the present invention to provide a process for preparing a supported hydrogenation catalyst with increased hydrogenation activity, without reducing the selectivity or the mechanical stability of the supported catalyst.

The object is achieved in accordance with the invention by a process for preparing a supported hydrogenation catalyst with increased hydrogenation activity, which comprises a hydrogenating metal and/or an oxide of a hydrogenating metal on an $Al_2O_3$-containing support material, said calcined supported hydrogenation catalyst being treated before or after the final shaping thereof and before use thereof in the hydrogenation with a base solution having a pH of >10 at a temperature in the range from 20 to 120° C. for 1 to 300 hours.

It has been found in accordance with the invention that, specifically in the case of supported hydrogenation catalysts which comprise aluminum oxide in the support material, the activity of the catalyst can be enhanced significantly by a base treatment at a pH of >10, without adversely affecting the selectivity and mechanical stability. This involves treatment with a base solution with a pH of >10 or at a pH of >10.

The term "supported hydrogenation catalyst" comprises catalysts which, as well as the hydrogenating metal or the hydrogenating metals, also comprise support materials. For example, the catalysts may be those in which the catalyst support is treated by impregnation with the hydrogenating metal. Likewise encompassed are catalysts which are prepared by coprecipitation, i.e. in which the hydrogenating metal or a salt or oxide thereof is precipitated together with the support material from precursor solutions. In general, the catalyst can be obtained by any suitable processes, provided that a hydrogenating metal and an $Al_2O_3$-containing support material are present alongside one another. The catalysts may be unsupported catalysts, impregnated catalysts, eggshell catalysts or precipitated catalysts. Suitable catalysts are described, for example, in WO 2007/006719, U.S. 2008/0299390, U.S. 2008/0071120 and U.S. Pat. No. 7,510,591.

The supported hydrogenation catalyst prepared in accordance with the invention comprises an $Al_2O_3$-containing support material. The support material preferably comprises more than 50% by weight and more preferably more than 75% by weight of $Al_2O_3$. It may be a pure $Al_2O_3$ support or an $Al_2O_3$-containing support material which additionally comprises, for example, further metal oxides such as cerium oxide, titanium dioxide, zirconium oxide, silicon dioxide and/or lanthanum oxide. In addition, the support, as well as aluminum, may also comprise other metals. Any remaining proportion preferably also comprises metal oxides.

The hydrogenating metal used may be all customary active metals used in hydrogenation catalysts. The hydrogenating metal is preferably selected from groups 8-11 of the periodic table of the chemical elements, more preferably from groups 10 and 11 of the periodic table of the chemical elements. The hydrogenating metal more preferably comprises copper, iron, nickel, rhodium, ruthenium, palladium or platinum, or is selected from these or mixtures thereof.

Especially for the hydrogenation of carbonyl compounds to the corresponding alcohols, supported copper catalysts are used industrially on a wide scale. Such catalysts, which can also be used in accordance with the invention, comprise the active material on the support material. The active material can be applied to an existing support material or else coprecipitated with the support material by any desired process.

In the preparation process according to the invention, the calcined supported hydrogenation catalyst is base-treated. A catalyst prepared, for example, by coprecipitation is typically washed, dried and calcined after the precipitation. This may be followed by a tableting or extrusion step and another calcination. In the case of catalysts produced by impregnation, the impregnation and drying are likewise followed by a calcination, which may in turn be followed by a further shaping step.

The catalyst material used in the process according to the invention has already been subjected to at least one of the calcination steps mentioned in the preceding preparation. The catalyst material may comprise catalysts already subjected to a final shaping, or catalyst powder obtained after the first calcination.

In the process according to the invention, treatment is effected with a base solution having a pH of >10, preferably >11, more preferably >12 and especially >13. The base solution which is used for treatment preferably has the pH mentioned, or the pH mentioned is present in the course of treatment of the catalyst with the base.

According to the invention, any suitable base solutions can be used. Preference is given to using aqueous, alcoholic or mixed aqueous/alcoholic base solutions. Examples of useful alcohols are alkanols, preferably $C_{1-4}$-alkanols such as methanol, ethanol, propanol, isopropanol or the butanols. In aqueous-alcoholic solutions, the alcohol component is preferably not more than 30% by weight, more preferably not more than 20% by weight and especially not more than 10% by weight. Particular preference is given to working with aqueous solutions.

The base used can be selected freely within a wide range. The base solution preferably comprises an alkali metal hydroxide or alkaline earth metal hydroxide or a mixture thereof. Particularly suitable alkali metal hydroxides are sodium hydroxide solution or potassium hydroxide solution. Particularly suitable alkaline earth metal hydroxides are magnesium hydroxide, calcium hydroxide and barium hydroxide.

The base solution more preferably comprises sodium hydroxide or potassium hydroxide, especially sodium hydroxide.

Particular preference is given to treatment with an aqueous sodium hydroxide solution.

The treatment with the base solution is effected by spraying the catalyst with the base solution or immersing the catalyst into a base solution, in which case the catalyst can simultaneously be moved mechanically. Preference is given to working with an amount of the base solution which is sufficient to completely cover the catalyst. The temperature in the course of treatment is in the range from 20 to 120° C., preferably 35 to 105° C., especially 50 to 100° C. The treatment time can be selected according to the base concentration or the pH and the temperature. It is generally in the range from 1 to 300 hours, preferably 5 to 200 hours, especially 10 to 150 hours.

Particular preference is given to treatment with aqueous 0.3 to 3.0 molar sodium hydroxide solution, particular preference to that with aqueous 0.5 to 2.0 molar sodium hydroxide solution. The pH is especially above 13.5 or above 14.

The treatment with the base solution can leach out a small portion of the aluminum oxide present in the support. Especially in the edge region of the shaped body treated, depletion of the aluminum oxide may take place. As a result of the treatment with the base solution, it is likewise possible for a portion of the aluminum oxide present in amorphous or x-ray-amorphous form to be converted to finely crystalline boehmite (AlOOH). These structural changes in the support material may be the origin of the enhanced activity.

The treatment with the base solution can reduce the aluminum content in the hydrogenation catalyst and/or in the calcined catalyst powder by 0 to 6% by weight, preferably 0.1 to 6% by weight, especially 0.1 to 3% by weight, calculated as elemental aluminum.

The rise in activity is not, as in the case of conventional Raney metal systems, attributable to the complete leaching-out of the metallic aluminum and the accompanying increase in the metal surface area. In the catalysts treated in accordance with the invention, only a significantly smaller portion of the aluminum, in the present case as aluminum oxide, aluminum oxide hydroxide and/or aluminum hydroxide, is leached out of the supported catalysts, for example tablets. This generally does not significantly alter the surface area of the hydrogenating metal.

Particular preference is given in accordance with the invention to treating catalysts which have been prepared as described in WO 2007/006719.

Such catalysts are prepared in a process in which
an oxidic material comprising copper oxide and aluminum oxide and at least one of the oxides of iron, lanthanum, tungsten, molybdenum, titanium, zirconium, tin or manganese is provided,
pulverulent metallic copper, copper flakes, pulverulent cement, graphite or a mixture thereof is added to the oxidic material,
the resulting mixture is shaped to a shaped body and
the shaped body is treated by the present process according to the invention.

The oxidic material more preferably comprises, based on the total weight of the oxidic material after calcination,
copper oxide with a proportion in the range of $50 \leq x \leq 80\%$ by weight, preferably $55 \leq x \leq 75\%$ by weight,
aluminum oxide with a proportion in the range of $15 \leq y \leq 35\%$ by weight, preferably $20 \leq y \leq 30\%$ by weight and
at least one of the oxides of iron, lanthanum, tungsten, molybdenum, titanium, zirconium, tin or manganese with a proportion in the range of $1 \leq z \leq 30\%$ by weight, preferably $2 \leq z \leq 25\%$ by weight,
where: $80 \leq x+y+z \leq 100$, especially $95 \leq x+y+z \leq 100$, cement not being included in the oxidic material in the above sense.

The proportion of the metallic copper added is preferably 1 to 40% by weight, based on the total weight of the oxidic material.

Graphite is added preferably in amounts of 0.5 to 5% by weight, based on the total weight of the oxidic material.

A preferred process according to the invention for preparing the starting catalyst will be described in detail hereinafter.

The catalyst used in the process according to the invention has the feature that the copper active component, the aluminum component and the component of at least one of the oxides of iron, lanthanum, tungsten, molybdenum, titanium, zirconium, tin or manganese are preferably precipitated simultaneously or successively with a sodium carbonate solution, then dried, calcined, tableted or extruded, and calcined once more.

In particular, the following precipitation methods are useful:
A) A copper salt solution, an aluminum salt solution and a solution of a salt of iron, lanthanum, tungsten, molybdenum, titanium, zirconium, tin or manganese, or a solution comprising copper salt, aluminium salt and a salt of iron, lanthanum, tungsten, molybdenum, titanium, zirconium, tin or manganese, is precipitated with a sodium carbonate solution in parallel or successively. The precipitated material is subsequently dried and optionally calcined.
B) Precipitation of a copper salt solution and of a solution of a salt of iron, lanthanum, tungsten, molybdenum, titanium, zirconium, tin or manganese, or of a solution comprising copper salt and at least one salt of iron, onto a prefabricated aluminum oxide support. In a particularly preferred embodiment, this is present in the form of a powder in an aqueous suspension. However, the support material may also be present in the form of spheres, extrudates, spall or tablets.
B1) In one embodiment (I), a copper salt solution and a solution of a salt of iron, lanthanum, tungsten, molybdenum, titanium, zirconium, tin or manganese, or a solution comprising copper salt and a salt of iron, lanthanum, tungsten, molybdenum, titanium, zirconium, tin or manganese, are preferably precipitated with sodium carbonate solution. The initial charge used is an aqueous suspension of the aluminum oxide support material.

Precipitated solids which result from A) or B) are filtered in a customary manner and preferably washed to free them of alkali, as described, for example, in DE 198 09 418.3.

Both the end products from A) and from B) are dried at temperatures of 50 to 150° C., preferably at 120° C., and subsequently, if appropriate, calcined preferably for 2 hours at generally 200 to 600° C., especially at 300 to 500° C.

The starting substances used for A) and/or B) may in principle be all Cu(I) and/or Cu(II) salts soluble in the solvents used in the application, for example nitrates, carbonates, acetates, oxalates or ammonium complexes, analogous aluminum salts and salts of iron, lanthanum, tungsten, molybdenum, titanium, zirconium, tin or manganese. For processes according to A) and B), particular preference is given to using copper nitrate.

In the process according to the invention, the above-described dried and optionally calcined powder is processed preferably to tablets, rings, ring tablets, extrudates, honeycombs or similar shaped bodies. For this purpose, all suitable processes from the prior art are conceivable. Particular preference is given to using a shaped catalyst body or a catalyst extrudate with a diameter d and a height h<5 mm, catalyst spheres with a diameter d of <6 mm or catalyst honeycombs with a cell diameter $r_z$<5 mm. The composition of the oxidic material is generally such that the proportion of copper oxide is in the range from 40 to 90% by weight, the proportion of oxides of iron, lanthanum, tungsten, molybdenum, titanium, zirconium, tin or manganese is in the range from 0 to 50% by weight, and the proportion of aluminum oxide is in the range of up to 50% by weight, based in each case on the total weight of the sum of the abovementioned oxidic constituents, these three oxides together constituting at least 80% by weight of the oxidic material after calcination, cement not being included in the oxidic material in the above sense.

After the inventive treatment with the base solution, the catalyst is preferably washed again, dried and optionally calcined once again.

The preferred catalyst as described above can be described in even more detail:

In general, pulverulent copper, copper flakes or pulverulent cement or graphite or a mixture thereof is added to the oxidic material in the range from 0.5 to 40% by weight, preferably in the range from 2 to 20% by weight and more preferably in the range from 3 to 18% by weight, based in each case on the total weight of the oxidic material.

The cement used is preferably an alumina cement. The alumina cement more preferably consists substantially of aluminum oxide and calcium oxide, and more preferably consists of from about 75 to 85% by weight of aluminum oxide and from about 15 to 25% by weight of calcium oxide. In addition, it is also possible to use a cement based on magnesium oxide/aluminum oxide, calcium oxide/silicon oxide and calcium oxide/aluminum oxide/iron oxide.

In particular, the oxidic material may have, in a proportion of at most 10% by weight, preferably at most 5% by weight, based on the total weight of the oxidic material, at least one further component which is selected from the group consisting of the elements Re, Fe, Ru, Co, Rh, Ir, Ni, Pd and Pt.

In a further preferred embodiment of the process according to the invention, graphite is added to the oxidic material before the shaping to the shaped body, in addition to the copper powder, the copper flakes or the cement powder or the mixture thereof.

Preference is given to adding sufficient graphite that the shaping to a shaped body can be carried out better. In a preferred embodiment, from 0.5 to 5% by weight of graphite, based on the total weight of the oxidic material, are added. It is immaterial whether graphite is added to the oxidic material before or after or simultaneously with the copper powder, the copper flakes or the cement powder or the mixture thereof.

After addition of the copper powder, of the copper flakes or of the cement powder or of the mixture thereof and, if appropriate, graphite to the oxidic material, the shaped body obtained after the shaping is optionally calcined at least once over a period of generally from 0.5 to 10 h, preferably from 0.5 to 2 hours. The temperature in this at least one calcination step is generally in the range from 200 to 600° C., preferably in the range from 250 to 500° C. and more preferably in the range from 270 to 400° C.

In the case of shaping with cement powder, it may be advantageous to moisten the shaped body obtained before the calcination with water and subsequently to dry it.

In the case of use as a catalyst in the oxidic form, the shaped body, before contacting with the hydrogenation solution, is pre-reduced with reducing gases, for example hydrogen, preferably hydrogen/inert gas mixtures, especially hydrogen/nitrogen mixtures, at temperatures in the range from 20 to 500° C., preferably in the range from 150 to 350° C. and especially in the range from 180 to 200° C. Preference is given to using a mixture having a hydrogen content in the range from 1 to 100% by volume, more preferably in the range from 1 to 50% by volume.

In a preferred embodiment, the inventive shaped body, before use as a catalyst, is activated in a manner known per se by treatment with reducing media. The activation is effected either beforehand in a reduction oven or after installation in the reactor. When the catalyst has been activated beforehand in the reduction oven, it is installed into the reactor and contacted with the hydrogenation solution directly under hydrogen pressure. According to the hydrogenating metal, as, for example, in the case of Cu or Ni, the activated catalyst is highly pyrophoric. Direct contact of the dry activated catalyst with air accordingly leads readily to damage to the catalyst and to a serious safety hazard. If the catalyst has been activated beforehand in a reduction oven, it is therefore advisable to blanket the activated catalyst with an inert solvent for transport and then to install it into the reactor in solvent-moist form. Suitable examples for this purpose are water, alcohols or moderately volatile to nonvolatile alkanes. Particularly advantageously, the transport to the reactor may be carried out in a substance intrinsic to the later process, for example the reactant (often a carbonyl compound) or the product (often an alcohol). Alternatively, the activated catalyst can also be transported and installed into the reactor under an inert gas, for example nitrogen or argon.

The preferred field of use of the shaped bodies prepared by the process according to the invention is the hydrogenation of organic compounds having carbonyl groups in a fixed bed. Other embodiments, for example the fluidized reaction with catalyst material in upward and downward motion, are, however, likewise possible. The hydrogenation can be performed in the gas phase or in the liquid phase. Preference is given to performing the hydrogenation in the liquid phase, for example in trickle mode or in liquid phase mode. When working in trickle mode, the liquid reactant comprising the carbonyl compound to be hydrogenated is allowed to trickle through the catalyst bed arranged in the reactor which is under hydrogen pressure, which forms a thin liquid film on the catalyst. In contrast, when working in liquid phase mode, hydrogen gas is introduced into the reactor flooded with the liquid reaction mixture, in the course of which the hydrogen passes through the catalyst bed in ascending gas bubbles.

In one embodiment, the solution to be hydrogenated is pumped through the catalyst bed in straight pass. In another embodiment of the process according to the invention, a portion of the product, after passing through the reactor, is drawn off continuously as the product stream and optionally passed through a second reactor, as defined above. The other portion of the product is fed back to the reactor together with fresh reactant comprising the carbonyl compound. This procedure is referred to hereinafter as circulation mode.

When trickle mode is selected as the embodiment of the process according to the invention, preference is given here to circulation mode. Preference is further given to working in circulation mode using a main reactor and postreactor.

The process according to the invention is suitable for hydrogenating carbonyl compounds, for example aldehydes and ketones, carboxylic acids, carboxylic esters, carboxylic anhydrides or lactones, to the corresponding alcohols, preference being given to aliphatic and cycloaliphatic, saturated and unsaturated carbonyl compounds. In the case of aromatic carbonyl compounds, undesired by-products may be formed by hydrogenation of the aromatic ring. The carbonyl compounds may bear further functional groups such as hydroxyl or amino groups. Unsaturated carbonyl compounds are generally hydrogenated to the corresponding saturated alcohols. The term "carbonyl compounds" as used in the context of the invention comprises all compounds which have a C=O group, including carboxylic acids and their derivatives. It will be appreciated that it is also possible to hydrogenate mixtures of two or more than two carbonyl compounds together. It is also possible for the individual carbonyl compound to be hydrogenated to comprise more than one carbonyl group.

Preference is given to using the process according to the invention for hydrogenating aliphatic aldehydes, hydroxy aldehydes, ketones, acids, esters, anhydrides, lactones and sugars.

Preferred aliphatic aldehydes are branched and unbranched, saturated and/or unsaturated aliphatic $C_2$-$C_{30}$ aldehydes, as are obtainable, for example, by oxo synthesis from linear or branched olefins with internal or terminal double bonds. It is also possible to hydrogenate oligomeric compounds which also comprise more than 30 carbonyl groups.

Examples of aliphatic aldehydes include:
formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylaldehyde, capraldehyde, glutaraldehyde.

In addition to the short-chain aldehydes mentioned, long-chain aliphatic aldehydes are also especially suitable, as can be obtained, for example, by oxo synthesis from linear α-olefins.

Particular preference is given to enalization products, for example 2-ethylhexenal, 2-methylpentenal, 2,4-diethyloctenal or 2,4-dimethylheptenal.

Preferred hydroxy aldehydes are $C_3$-$C_{12}$ hydroxy aldehydes, as are obtainable, for example, by aldol reaction from aliphatic and cycloaliphatic aldehydes and ketones with themselves or formaldehyde. Examples are 3-hydroxypropanal, dimethylolethanal, trimethylolethanal (pentaerythrital), 3-hydroxybutanal (acetaldol), 3-hydroxy-2-ethylhexanal (butylaldol), 3-hydroxy-2-methylpentanal (propionaldol), 2-methylol-propanal, 2,2-dimethylolpropanal, 3-hydroxy-2-methylbutanal, 3-hydroxypentanal, 2-methylolbutanal, 2,2-dimethylolbutanal (DMB), hydroxypivalaldehyde. Particular preference is given to hydroxypivalaldehyde (HPA) and dimethylolbutanal (DMB).

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, 2,3-butanedione, 2,4-pentanedione, 2,5-hexanedione and methyl vinyl ketone.

It is also possible to convert carboxylic acids and derivatives thereof, preferably those having 1-20 carbon atoms. The following should be mentioned in particular:
carboxylic acids, for example formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexanecarboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-amino-benzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic esters, for example the $C_1$-$C_{12}$-alkyl esters of the abovementioned carboxylic acids, especially methyl formate, ethyl acetate, butyl butyrate, dialkyl phthalates, dialkyl isophthalates, dialkyl terephthalates, dialkyl adipates, dialkyl maleates, for example the dimethyl esters of these acids, methyl (meth)acrylate, butyrolactone, caprolactone and polycarboxylic esters, for example polyacrylic and polymethacrylic esters and their copolymers and polyesters, for example polymethyl methacrylate, terephthalic esters and other industrial plastics, in which case hydrogenolyses, i.e. the conversion of esters to the corresponding acids and alcohols, are carried out in particular;

fats;

carboxylic anhydrides, for example the anhydrides of the abovementioned carboxylic acids, especially acetic anhydride, propionic anhydride, benzoic anhydride and maleic anhydride;

carboxamides, for example formamide, acetamide, propionamide, stearamide, terephthalamide.

It is also possible to convert hydroxycarboxylic acids, for example lactic acid, malic acid, tartaric acid or citric acid, or amino acids, for example glycine, alanine, proline and arginine, and peptides.

Particularly preferred organic compounds to be hydrogenated are saturated or unsaturated carboxylic acids, carboxylic esters, carboxylic anhydrides, aldehydes or lactones or mixtures of two or more thereof.

Accordingly, the present invention also relates to a process as described above, wherein the organic compound is a carboxylic acid, a carboxylic ester, a carboxylic anhydride, an aldehyde or a lactone.

Examples of these compounds include maleic acid, maleic anhydride, succinic acid, succinic anhydride, adipic acid, 6-hydroxycaproic acid, 2-cyclododecylpropionic acid, the esters of the aforementioned acids, for example methyl, ethyl, propyl or butyl esters. Further examples are hydroxypivalaldehyde (HPA), dimethylolbutanal (DMB), γ-butyrolactone and caprolactone.

In a very particularly preferred embodiment, the present invention relates to a process as described above, wherein the organic compound is adipic acid or an adipic ester or a mixture thereof.

The carbonyl compound to be hydrogenated can be fed to the hydrogenation reactor alone or as mixture with the product of the hydrogenation reaction, in which case this can take place in undiluted form or with use of additional solvent. Suitable additional solvents are in particular water, alcohols such as methanol, ethanol and the alcohol formed under the reaction conditions. Preferred solvents are water, THF and NMP; particular preference is given to water.

The hydrogenation, both in trickle and liquid phase mode, each preferably being carried out in circulation mode, is generally carried out at a temperature in the range from 50 to 350° C., preferably in the range from 70 to 300° C., more preferably in the range from 100 to 270° C., and a pressure in the range from 3 to 350 bar, preferably in the range from 5 to 330 bar, more preferably in the range from 10 to 300 bar.

In a very particularly preferred embodiment, the catalysts of the invention are employed in processes for preparing hexanediol and/or caprolactone, as described in DE 196 07 954, DE 196 07 955, DE 196 47 348 and DE 196 47 349.

The process according to the invention achieves high conversions and selectivities using the catalysts of the invention. At the same time, the catalysts of the invention have high chemical and mechanical stability.

The invention also relates to supported hydrogenation catalysts which are obtainable by the process described above.

The invention additionally relates to the use of a supported hydrogenation catalyst as obtainable in accordance with the invention for hydrogenating organic compounds having carbonyl groups. The organic compound is preferably a carboxylic acid, a carboxylic ester, a carboxylic anhydride, an aldehyde or a lactone.

The invention likewise relates to a process for hydrogenating organic compounds having carbonyl groups over a hydrogenation catalyst, wherein a supported hydrogenation catalyst obtainable as described above is used.

Preference is given to performing the process in fixed bed reactors at hydrogen pressures around 200 bar and temperatures around 200° C. Typically, conversions of more than 99.5% are achieved with catalyst hourly space velocities of not more than 0.1 to 0.6 kg/(l*h). Use of the inventive catalysts can in some cases allow the catalyst hourly space velocity to be tripled up to 1.8 kg/(l*h), with no observed decline in conversion (to less than 99.5%). This did not adversely affect the selectivity or the mechanical stability of the shaped bodies.

The invention is illustrated in detail by examples.

EXAMPLES

In the examples, a $Cu/Al_2O_3/La_2O_3$ catalyst according to WO 2007/006719, example 1, is used in the form of tablets of dimensions 1.5×1.5 mm or 3×3 mm. The example reaction selected was the hydrogenation of dimethyl adipate to 1,6-hexanediol. In addition, the hydrogenation of dimethylolbutanal (DMB) to trimethylolpropane was also examined.

The mechanical stability of the solid-state catalysts was determined via the side crushing strength. The side crushing strength was determined with a Z 2.5/T 919 instrument from Zwick Röll (Ulm).

1. Preparation of the Catalysts:

Comparative Example

The preparation corresponds to example 1 from WO 2007/006719 A1. Tabletting is effected with addition of 3% by weight of graphite and 15% by weight of copper flakes to give 1.5×1.5 mm tablets.

The catalyst thus prepared comprises 56% by weight of Cu element, 11.3% by weight of Al element and 3.2% by weight of La element. The side crushing strength in the oxidic and unused state is on average 67 N.

Example 1

685 g of catalyst tablets according to the comparative example are treated at room temperature with 1000 ml of 0.5 M NaOH over 48 h. The deinstalled catalyst tablets are subsequently washed to neutrality with distilled water and dried at 120° C. for 16 hours. The catalyst thus prepared comprises 53% by weight of Cu element, 10.3% by weight of Al element and 3.1% by weight of La element. The side crushing strength in the oxidic and unused state is an average of 69 N.

Example 2

1500 g of catalyst powder according to the comparative example (same method, without precompaction and tabletting) are stirred in suspension with 6000 ml of 2.0 M NaOH at 50° C. over 126 hours. The hot suspension is filtered undiluted and washed to neutrality with cold distilled water. The filtercake was dried at 120° C. for 16 hours. The dry filtercake was passed through a 0.8 mm screen and pressed with 3% graphite and 15% copper flakes to 1.5×15 mm tablets. The tablets were postcalcined at 350° C. over 2 hours. The catalyst thus prepared comprises 59% by weight of Cu element, 6.9% by weight of Al element and 3.6% by weight of La element. The side crushing strength in the oxidic and unused state is on average 46 N.

Activation:

All catalysts were reduced with an $N_2/H_2$ mixture at 1 bar and a temperature of 180° C. in a procedure familiar to the person skilled in the art.

II. Hydrogenation of Dimethyl Adipate to 1,6-Hexanediol

Comparative Example 200 ml of the catalyst prepared according to the comparative example were charged in activated form into a jacketed oil-heated tubular reactor (diameter 14 mm). At 200° C., hydrogen pressure 200 bar and a hydrogen feed of 200 l (STP)/h, dimethyl adipate was metered in continuously at different feed rates. The reactor was operated in single pass. It was possible to operate the reactor in a WHSV range of up to 0.6 g/(ml*h) with ester conversions of >99.5% and 1,6-hexanediol selectivities of >99.7%.

| WHSV g/(ml*h) | Conversion % | Selectivity % |
|---|---|---|
| 0.3 | 99.86 | 99.20 |
| 0.4 | 99.82 | 99.51 |
| 0.6 | 99.58 | 99.70 |
| 0.7 | 99.35 | 99.77 |
| 0.8 | 98.68 | 99.77 |
| 0.9 | 98.26 | 99.80 |
| 1.0 | 97.00 | 99.81 |

Example 1

160 ml of the catalyst prepared according to example 1 were introduced in activated form into a jacketed oil-heated tubular reactor (diameter 14 mm). At 200° C., hydrogen pressure 200 bar and a hydrogen feed of 200 l (STP)/h, dimethyl adipate was metered in continuously at different feed rates. The reactor was operated in single pass. It was possible to operate the reactor in a WHSV range of up to 1.8 g/(ml*h) with ester conversions of >99.7% and 1,6-hexanediol selectivities of >99.5.

| WHSV g/(ml*h) | Conversion % | Selectivity % |
|---|---|---|
| 0.4 | 99.86 | 98.93 |
| 0.7 | 99.85 | 99.32 |
| 1.1 | 99.84 | 99.60 |
| 1.5 | 99.82 | 99.69 |
| 1.8 | 99.69 | 99.71 |

Example 2

200 ml of the catalyst prepared according to example 2 were introduced in activated form into a jacketed oil-heated tubular reactor (diameter 14 mm). At 200° C., hydrogen pressure 200 bar and a hydrogen feed of 200 l (STP)/h, dimethyl adipate was metered in continuously at different feed rates. The reactor was operated in single pass. It was possible to operate the reactor in a WHSV range of up to 1.5 g/(ml*h) with ester conversions of >99.8% and 1,6-hexanediol selectivities of >99.8.

| WHSV g/(ml*h) | Conversion % | Selectivity % |
|---|---|---|
| 0.5 | 99.85 | 99.46 |
| 0.7 | 99.86 | 99.57 |
| 1.1 | 99.88 | 99.74 |
| 1.3 | 99.84 | 99.84 |
| 1.5 | 99.82 | 99.85 |

III. Hydrogenation of Dimethylolbutyraldehyde (DMB) to Trimethylolpropane (IMP)

Comparative Example 150 ml of the catalyst prepared according to the comparative example were activated and introduced into an oil-heated jacketed tubular reactor. At 100° C. and hydrogen pressure 90 bar, a 70% aqueous DMB solution was metered in continuously at different feed rates. The reactor was operated with a circulation to feed ratio of 6:1. It was possible to operate the system in an LHSV range up to 0.2 ml/(ml*h) with aldehyde conversions of >99.6% and TMP selectivities of >96%.

| LHSV ml/(ml*h) | Conversion % | Selectivity % |
|---|---|---|
| 0.20 | 99.69 | 96.68 |
| 0.42 | 97.47 | 97.08 |
| 0.50 | 95.29 | 96.96 |

Example 1

150 ml of the catalyst prepared according to example 1 were activated and introduced into an oil-heated jacketed tubular reactor. At 100° C. and hydrogen pressure 90 bar, a 70% aqueous DMB solution was metered in continuously at different feed rates. The reactor was operated with a circulation to feed ratio of 6:1. It was possible to operate the reactor in an LHSV range up to 0.5 ml/(ml*h) with ester conversions of >99.9% and TMP selectivities of >95%.

| LHSV ml/(ml*h) | Conversion % | Selectivity % |
|---|---|---|
| 0.20 | 99.99 | 95.22 |
| 0.42 | 99.96 | 95.30 |
| 0.50 | 99.92 | 95.21 |

The invention claimed is:

1. A process for preparing a supported hydrogenation catalyst with increased hydrogenation activity, which comprises a hydrogenating metal and an oxide of a hydrogenating metal on an $Al_2O_3$-containing support material, said calcined supported hydrogenation catalyst being treated before or after the final shaping thereof and before use thereof in the hydrogenation with a base solution having a pH of >10 at a temperature in the range from 20 to 120° C. for 1 to 300 hours, and wherein an oxidic material comprising copper oxide and aluminum oxide and at least one of the oxides of iron, lanthanum, tungsten, molybdenum, titanium, zirconium, tin or manganese is provided, pulverulent metallic copper, copper flakes, pulverulent cement, graphite or a mixture thereof is added to the oxidic material and the resulting mixture is shaped to a shaped body.

2. The process according to claim 1, wherein the base solution comprises an alkali metal hydroxide or alkaline earth metal hydroxide or a mixture thereof.

3. The process according to claim 2, wherein the base solution comprises sodium hydroxide.

4. The process according to claim 1, wherein treatment is effected with an aqueous base solution.

5. The process according to claim 1, wherein the hydrogenating metal is selected from groups 8-11 of the periodic table of the chemical elements.

6. The process according to claim 1, wherein the hydrogenating metal is Cu, Fe, Ni, Rh, Ru, Pd, Pt or mixtures thereof.

7. The process according to claim 6, wherein the hydrogenating metal comprises copper.

8. The process according to claim 1, wherein the base solution comprises sodium hydroxide.

9. The process according to claim 2, wherein treatment is effected with an aqueous base solution.

10. The process according to claim 2, wherein the hydrogenating metal is selected from groups 8-11 of the periodic table of the chemical elements.

11. The process according to claim 2, wherein the hydrogenating metal is Cu, Fe, Ni, Rh, Ru, Pd, Pt or mixtures thereof.

12. The process according to claim 3, wherein the hydrogenating metal comprises copper.

* * * * *